(12) United States Patent
Sankaranarayanan et al.

(10) Patent No.: US 11,651,839 B2
(45) Date of Patent: May 16, 2023

(54) SYSTEMS AND METHODS FOR GENERATING PHASE DIAGRAMS FOR METASTABLE MATERIAL STATES

(71) Applicant: UCHICAGO ARGONNE, LLC, Chicago, IL (US)

(72) Inventors: Subramanian Sankaranarayanan, Naperville, IL (US); Troy David Loeffler, Chicago, IL (US); Henry Chan, Schaumburg, IL (US); Mathew J. Cherukara, Darien, IL (US); Srilok Srinivasan, Woodridge, IL (US)

(73) Assignee: UChicago Argonne, LLC, Chicago, IL (US)

( * ) Notice: Subject to any disclaimer, the term of this patent is extended or adjusted under 35 U.S.C. 154(b) by 395 days.

(21) Appl. No.: 16/807,081

(22) Filed: Mar. 2, 2020

(65) Prior Publication Data
US 2021/0272658 A1    Sep. 2, 2021

(51) Int. Cl.
*G16C 20/30* (2019.01)
*G16C 20/80* (2019.01)
*G16C 20/00* (2019.01)
*G16C 20/70* (2019.01)

(52) U.S. Cl.
CPC ............. *G16C 20/30* (2019.02); *G16C 20/00* (2019.02); *G16C 20/80* (2019.02); *G16C 20/70* (2019.02)

(58) Field of Classification Search
CPC .... G16C 20/80; G16C 60/00; G16K 9/00147; G16N 20/00
USPC .......................................................... 703/12
See application file for complete search history.

(56) References Cited

U.S. PATENT DOCUMENTS

| | | | |
|---|---|---|---|
| 6,128,609 | A | 10/2000 | Rose |
| 6,882,739 | B2 | 4/2005 | Kurtz et al. |
| 7,672,815 | B2 | 3/2010 | Asgari et al. |
| 7,680,557 | B2 | 3/2010 | Kim et al. |
| 8,117,141 | B1 | 2/2012 | Srinivasa et al. |

(Continued)

FOREIGN PATENT DOCUMENTS

| | | |
|---|---|---|
| CN | 107563574 A | 1/2018 |
| CN | 108280207 A | 7/2018 |

(Continued)

OTHER PUBLICATIONS

Abascal & Vega, "A general purpose model for the condensed phases of water: TIP4P/2005," Journal of Chemical Physics 123(23), 234505, 12 pages (2005).

(Continued)

*Primary Examiner* — Thinh T Nguyen
(74) *Attorney, Agent, or Firm* — Foley & Lardner LLP

(57) ABSTRACT

A system can include one or more processors configured to access at least one parameter of a material, generate a plurality of structures of the material using the at least one parameter, determine a state of each structure of the plurality of structures using the at least one parameter, determine a difference between the state of each structure of the plurality of structures and a ground state value, evaluate a convergence condition responsive to determining the difference between the state of each structure of the plurality of structures and the ground state value, and output at least one structure of the plurality of structures responsive to the convergence condition being satisfied.

9 Claims, 4 Drawing Sheets

(56) References Cited

U.S. PATENT DOCUMENTS

| | | | |
|---|---|---|---|
| 8,219,511 | B2 | 7/2012 | Yang et al. |
| 8,835,895 | B2 | 9/2014 | Sumino et al. |
| 8,871,670 | B2 | 10/2014 | Seebauer |
| 8,932,347 | B2 | 1/2015 | Choubey et al. |
| 9,175,174 | B2 | 11/2015 | Kambe |
| 9,525,032 | B2 | 12/2016 | Slack et al. |
| 9,683,682 | B2 | 6/2017 | Narayanan et al. |
| 9,727,824 | B2 | 8/2017 | Rose et al. |
| 9,731,371 | B2 | 8/2017 | Enyedy et al. |
| 9,823,737 | B2 | 11/2017 | Mazed et al. |
| 9,833,862 | B2 | 12/2017 | Denney et al. |
| 9,839,978 | B2 | 12/2017 | Narayanan et al. |
| 9,914,765 | B2 | 3/2018 | Timmer et al. |
| 9,937,580 | B2 | 4/2018 | Peters et al. |
| 10,023,795 | B2 | 7/2018 | Ning |
| 10,046,419 | B2 | 8/2018 | Denney et al. |
| 10,052,706 | B2 | 8/2018 | Henry et al. |
| 10,052,707 | B2 | 8/2018 | Henry et al. |
| 10,068,973 | B2 | 9/2018 | Slack et al. |
| 10,087,079 | B2 | 10/2018 | Steiner et al. |
| 10,419,655 | B2 | 9/2019 | Sivan |
| 10,529,003 | B2 | 1/2020 | Mazed |
| 10,584,916 | B2 | 3/2020 | Gan et al. |
| 11,501,210 | B1 | 11/2022 | Zhdanov et al. |
| 2003/0217026 | A1 | 11/2003 | Teig et al. |
| 2013/0159206 | A1 | 6/2013 | Barahona et al. |
| 2015/0081599 | A1 | 3/2015 | Dobler |
| 2015/0106035 | A1 | 4/2015 | Vecchio et al. |
| 2015/0199607 | A1 | 7/2015 | Fang |
| 2016/0179162 | A1 | 6/2016 | Eastep et al. |
| 2017/0261949 | A1 | 9/2017 | Hoffmann et al. |
| 2017/0285123 | A1 | 10/2017 | Kaditz |
| 2018/0136356 | A1 | 5/2018 | Wilson et al. |
| 2018/0165603 | A1 | 6/2018 | Van Seijen et al. |
| 2018/0240031 | A1 | 8/2018 | Huszar et al. |
| 2018/0361514 | A1 | 12/2018 | Narayanan et al. |
| 2019/0050628 | A1* | 2/2019 | Sankaranarayanan .............. G06K 9/00147 |
| 2019/0279094 | A1 | 9/2019 | Baughman et al. |
| 2019/0370955 | A1 | 12/2019 | Zhang et al. |
| 2020/0042776 | A1 | 2/2020 | Shen et al. |
| 2020/0250491 | A1 | 8/2020 | Peng et al. |
| 2021/0042609 | A1 | 2/2021 | Owoyele et al. |
| 2021/0089921 | A1 | 3/2021 | Aghdasi et al. |
| 2021/0174215 | A1 | 6/2021 | Chan et al. |
| 2021/0233191 | A1 | 7/2021 | Shin et al. |
| 2022/0101828 | A1 | 3/2022 | Fukutomi et al. |

FOREIGN PATENT DOCUMENTS

| | | |
|---|---|---|
| CN | 108304679 A | 7/2018 |
| CN | 108427939 A | 8/2018 |
| CN | 108896943 A | 11/2018 |
| CN | 109146064 A | 1/2019 |
| CN | 109657793 A | 4/2019 |
| CN | 109918684 A | 6/2019 |
| CN | 109920501 A | 6/2019 |
| CN | 110619527 A | 12/2019 |
| CN | 110737824 A | 1/2020 |
| CN | 110745136 A | 2/2020 |
| CN | 110879951 A | 3/2020 |
| WO | WO-2019/012279 A1 | 7/2018 |

OTHER PUBLICATIONS

Abascal & Vega, "A general purpose model for the condensed phases of water: TIP4P/2005," The Journal of Chemical Physics 123, 234505, 12 pages (2005).

Abascal, et al., "A potential model for the study of ices and amorphous water: TIP4P/Ice," Journal of Chemical Physics 122(23), 234511, 9 pages (2005).

Agarwal, et al., "Thermodynamic, Diffusional, and Structural Anomalies in Rigid-Body Water Models," Journal of Physical Chemistry B 115(21), pp. 6935-6945 (2011).

Agarwal, et al., "Thermodynamic, Diffusional, and Structural Anomalies in Rigid-Body Water Models," The Journal of Physical Chemistry C 115(21), pp. 6935-6945 (2011).

Amaya, et al., "How Cubic Can Ice Be?," The Journal of Physical Chemistry Letters 8(14), pp. 3216-3222 (2017).

Berendsen, et al., "The missing term in effective pair potentials," Journal of Physical Chemistry 91(24), pp. 6269-6271 (1987).

Bigg & Hopwood, "Ice Nuclei in the Antarctic," Journal of the Atmospheric Sciences 20(3), pp. 185-188 (1963).

Blackford, "Sintering and microstructure of ice: a review," Journal of Physics D: Applied Physics 40(21), pp. R355-R385 (2007).

Boulton & Hindmarsh, "Sediment deformation beneath glaciers: Rheology and geological consequences," Journal of Geophysical Research: Solid Earth 92(B9), pp. 9059-9082 (1987).

Budd & Jacka, "A review of ice rheology for ice sheet modelling," Cold Regions Science & Technology 16(2), pp. 107-144 (1989).

Chickos & Acree, "Enthalpies of Sublimation of Organic and Organometallic Compounds. 1910-2001," Journal of Physical and Chemical Reference Data 31(2), pp. 537-698 (2002).

Chickos & Acree, "Enthalpies of Sublimation of Organic and Organometallic Compounds. 1910-2001," Journal of Physical and Chemical Reference Data 31, 537 (2002).

Darre, et al., "Coarse-grained models of water," WIREs Computational Molecular Science 2(6), pp. 921-930 (2012).

Demott, et al., "Predicting global atmospheric ice nuclei distributions and their impacts on climate," Proceedings of the National Academy of Sciences 107(25), pp. 11217-11222 (2010).

Doran, et al., "Climate forcing and thermal feedback of residual lake-ice covers in the high Arctic," Limnology & Oceanography 41(5), pp. 839-848 (1996).

Durand, et al., "Deformation of grain boundaries in polar ice," Europhysics Letters 67(6), pp. 1038-1044 (2004).

Durham & Stern, "Rheological Properties of Water Ice—Applications to Satellites of the Outer Planets," Annual Review of Earth and Planetary Sciences 29, pp. 295-330 (2001).

Durham, et al., "Effects of dispersed particulates on the rheology of water ice at planetary conditions," Journal of Geophysical Research: Planets 97(E12), pp. 20883-20897 (1992).

Engel, et al., "Anharmonic Nuclear Motion and the Relative Stability of Hexagonal and Cubic ice," Physical Review X 5, 021033, 10 pages (2015).

Espinosa, et al., "Ice-Water Interfacial Free Energy for the TIP4P, TIP4P/2005, TIP4P/Ice, and mW Models As Obtained from the Mold Integration Technique," The Journal of Physical Chemistry C120(15), pp. 8068-8075 (2016).

Espinosa, et al., "The mold integration method for the calculation of the crystal-fluid interfacial free energy from simulations," The Journal of Chemical Physics 141, 134709, 16 pages (2014).

Ester, et al., "A density-based algorithm for discovering clusters a density-based algorithm for discovering clusters in large spatial databases with noise," Proceedings of the Second International Conference on Knowledge Discovery and Data Mining, pp. 226-231 (1996).

Ester, et al., "A Density-Based Algorithm for Discovering Clusters in Large Spatial Databases with Noise," Proceedings of the Second International Conference on Knowledge Discovery and Data Mining, pp. 226-231 (1996).

Faken, et al., "Systematic analysis of local atomic structure combined with 3D computer graphics," Computational Materials Science, vol. 2, Issue 2, pp. 279-286 (Mar. 1994).

Faria, et al., "The microstructure of polar ice. Part 1: Highlights from ice core research," Journal of Structural Geology 61, pp. 2-20 (2014).

Fisher & Koerner, "On the Special Rheological Properties of Ancient Microparticle-Laden Northern Hemisphere Ice as Derived from Bore-Hole and Core Measurements," Journal of Glaciology 32(112), pp. 501-510 (1986).

Ghormley, "Enthalpy Changes and Heat-Capacity Changes in the Transformations from High-Surface-Area Amorphous Ice to Stable Hexagonal Ice," The Journal of Chemical Physics 48, pp. 503-508 (1968).

(56) References Cited

OTHER PUBLICATIONS

Gillen, et al., "Self-Diffusion in Liquid Water to −31 C," Journal of Chemical Physics 57(12), pp. 5117-5119 (1972).
Gillen, et al., "Self-Diffusion in Liquid Water to −31C," The Journal of Chemical Physics 57, pp. 5117-5119 (1972).
Gow & Williamson, "Rheological implications of the internal structure and crystal fabrics of the West Antarctic ice sheet as revealed by deep core drilling at Byrd Station," Geological Society of America Bulletin 87(12), pp. 1665-1677 (1976).
Gow, et al., "Physical and structural properties of the Greenland Ice Sheet Project 2 ice core: A review," Journal of Geophysical Research: Oceans 102(C12), pp. 26559-26575 (1997).
Grenfell, et al., "Reflection of solar radiation by the Antarctic snow surface at ultraviolet, visible, and near-infrared wavelengths," Journal of Geophysical Research: Atmospheres 99(D9), pp. 18669-18684 (1994).
Hadley & Mccabe, "Coarse-grained molecular models of water: a review," Molecular Simulation 38(8-9), pp. 671-681 (2012).
Haji-Akbari & Debenedetti, "Direct calculation of ice homogeneous nucleation rate for a molecular model of water," Proceedings of the National Academy of Sciences 112(34), pp. 10582-10588 (2015).
Handel, et al., "Direct Calculation of Solid-Liquid Interfacial Free Energy for Molecular Systems: TIP4P Ice-Water Interface," Physical Review Letters 100, 036104, 4 pages (2008).
Hansen, et al., "Modelling Ice Ic of Different Origin and Stacking-Faulted Hexagonal Ice Using Neutron Powder Diffraction Data," Physics and Chemistry of Ice: Proceedings of the 11th International Conference, pp. 201-208 (2007).
Henkelman & Jonsson, "Improved tangent estimate in the nudged elastic band method for finding minimum energy paths and saddle points," The Journal of Chemical Physics 113, pp. 9978-9985 (2000).
Henkelman, et al., "A climbing image nudged elastic band method for finding saddle points and minimum energy paths," The Journal of Chemical Physics 113, pp. 9901-9940 (2000).
Holz, et al., "Temperature-dependent self-diffusion coefficients of water and six selected molecular liquids for calibration in accurate 1H NMRPFG measurements," Physical Chemistry Chemical Physics 2(20), pp. 4740-4742 (2000).
Hondoh, "Dislocation mechanism for transformation between cubic ice Ic and hexagonal ice Ih," Philosophical Magazine 95(32), pp. 3590-3620 (2015).
Hondoh, et al., "Formation and annihilation of stacking faults in pure ice," The Journal of Physical Chemistry 87(21), pp. 4040-4044 (1983).
Horn, et al., "Development of an improved four-site water model for biomolecular simulations: TIP4P-Ew," Journal of Chemical Physics 120(20), pp. 9665-9678 (2004).
Hudait, et al., "Free energy contributions and structural characterization of stacking disordered ices," Physical Chemistry Chemical Physics 18(14), pp. 9544-9553 (2016).
Jacobson, et al., "How Short Is Too Short for the Interactions of a Water Potential? Exploring the Parameter Space of a Coarse-Grained Water Model Using Uncertainty Quantification," The Journal of Physical Chemistry B 118(28), pp. 8190-8202 (2014).
Johnston & Molinero, "Crystallization, Melting, and Structure of Water Nanoparticles at Atmospherically Relevant Temperatures," Journal of the American Chemical Society 134(15), pp. 6650-6659 (2012).
Jorgensen & Madura, "Temperature and size dependence for Monte Carlo simulations of TIP4P water," Molecular Physics 56(6), pp. 1381-1392 (1985).
Jorgensen & Tirado-Rives, "Potential energy functions for atomic-level simulations of water and organic and biomolecular systems," Proceedings of the National Academy of Sciences 102(19), pp. 6665-6670 (2005).
Jorgensen, et al., "Comparison of simple potential functions for simulating liquid water," Journal of Chemical Physics 79, pp. 926-935 (1983).

Ketcham & Hobbs, "An experimental determination of the surface energies of ice," The Philosophical Magazine: A Journal of Theoretical Experimental and Applied Physics 19(162), pp. 1161-1173 (1969).
Kokhanovsky, et al., "Reflective properties of natural snow: approximate asymptotic theory versus in situ measurements," IEEE Transactions on Geoscience and Remote Sensing 43(7), pp. 1529-1535 (2005).
Kuhs, et al., "Extent and relevance of stacking disorder in 'ice Ic'," Proceedings of the National Academy of Sciences 109(52), pp. 21259-21264 (2012).
Kuo, et al., "Liquid Water from First Principles: Investigation of Different Sampling Approaches," The Journal of Physical Chemistry B 108(34), pp. 12990-12998 (2004).
Lee, "Temperature Dependence on Structure and Self-Diffusion of Water: A Molecular Dynamics Simulation Study using SPC/E Model," Bulletin of the Korean Chemical Society 34(12), pp. 3800-3804 (2013).
Li, et al., "Freeze casting of porous materials: review of critical factors in microstructure evolution," International Materials Review 57(1), pp. 37-60 (2013).
Liu, et al., "Direct Measurement of Critical Nucleus Size in Confined Volumes," Langmuir 23(13), pp. 7286-7292 (2007).
Lu, et al., "Coarse-Graining of TIP4P/2005, TIP4P-Ew, SPC/E, and TIP3P to Monatomic Anisotropic Water Models Using Relative Entropy Minimization," Journal of Chemical Theory and Computation 10(9), pp. 4104-4120 (2014).
Lupi, et al., "Role of stacking disorder in ice nucleation," Nature 551, pp. 218-222 (2017).
Mahoney & Jorgensen, "A five-site model for liquid water and the reproduction of the density anomaly by rigid, nonpolarizable potential functions," Journal of Chemical Physics 112(20), pp. 8910-8922 (2000).
Mahoney & Jorgensen, "A five-site model for liquid water and the reproduction of the density anomaly by rigid, nonpolarizable potential functions," The Journal of Chemical Physics 112, pp. 8910-8922 (2000).
Majewski, et al., "Toward a Determination of the Critical Size of Ice Nuclei. A Demonstration by Grazing Incidence X-ray Diffraction of Epitaxial Growth of Ice under the C31H63OH Alcohol Monolayer," Journal of Physical Chemistry 98(15), pp. 4087-4093 (1994).
Malkin, et al., "Stacking disorder in ice I," Physical Chemistry Chemical Physics 17(1), pp. 60-76 (2015).
Malkin, et al., "Structure of ice crystallized from supercooled water," Proceedings of the National Academy of Sciences 109(4), pp. 1041-1045 (2012).
Mangold, et al., "Experimental and theoretical deformation of ice-rock mixtures: Implications on rheology and ice content of Martian permafrost," Planetary and Space Science 50(4), pp. 385-401 (2002).
Maras, et al., "Global transition path search for dislocation formation in Ge on Si(001)," Cornell University Library Materials Science, 29 pages (Jan. 25, 2016).
Maras, et al., "Global transition path search for dislocation formation in Ge on Si(001)," Computer Physics Communications 205, pp. 13-21 (2016).
Marrone & Car, "Nuclear Quantum Effects in Water," Physical Review Letters 101, 017801, 4 pages (2008).
Mcmillan & Los, "Vitreous Ice: Irreversible Transformations During Warm-Up," Nature 206, pp. 806-807 (1965).
Molinero & Moore, "Water Modeled As an Intermediate Element between Carbon and Silicon," The Journal of Physical Chemistry B 113(13), pp. 4008-4016 (2009).
Montagnant & Duval, "The viscoplastic behaviour of ice in polar ice sheets: experimental results and modelling," Comptes Rendus Physique 5(7), pp. 699-708 (2004).
Montagnat & Duval, "Rate controlling processes in the creep of polar ice, influence of grain boundary migration associated with recrystallization," Earth and Planetary Science Letters 183(1-2), pp. 179-186 (2000).
Montagnat, et al., "Lattice distortion in ice crystals from the Vostok core (Antarctica) revealed by hard X-ray diffraction; implication in

(56) References Cited

OTHER PUBLICATIONS the deformation of ice at low stresses," Earth and Planetary Science Letters 214(1-2), pp. 369-378 (2003).
Moore & Molinero, "Is it cubic? Ice crystallization from deeply supercooled water," Physical Chemistry Chemical Physics 13(44), pp. 20008-20016 (2011).
Moore & Molinero, "Ice crystallization in water's 'no-man's land'," Journal of Chemical Physics 132, 244504 (2010).
Murray et al., "The formation of cubic ice under conditions relevant to Earth's atmosphere," Nature 434, pp. 202-205 (2005).
Nada & Van Der Eerden, "An intermolecular potential model for the simulation of ice and water near the melting point: A six-site model of H2O," Journal of Chemical Physics 118(16), pp. 7401-7413 (2003).
Nakano, "A space-time-ensemble parallel nudged elastic band algorithm for molecular kinetics simulation," Computer Physics Communications 178(4), pp. 280-289 (2008).
Narten, et al., "Diffraction pattern and structure of amorphous solid water at 10 and 77 K," Journal of Chemical Physics 64, pp. 1106-1121 (1976).
Narten, et al., "Diffraction pattern and structure of amorphous solid water at 10 and 77K," The Journal of Chemical Physics 64, pp. 1106-1121 (1976).
Nelder & Mead, "A Simplex Method for Function Minimization," The Computer Journal 7(4), pp. 308-313 (1965).
Orsi, et al., "Comparative assessment of the ELBA coarse-grained model for water," Molecular Physics 112(11), pp. 1566-1576 (2014).
Perovich & Elder, "Temporal evolution of Arctic sea-ice temperature," Annals of Glaciology 33, pp. 207-211 (2001).
Perovich, et al., "Variability in Arctic sea ice optical properties," Journal of Geophysical Research: Oceans 103(C1), pp. 1193-1208 (1998).
Petrovic, "Review Mechanical properties of ice and snow," Journal of Materials Science 38(1), pp. 1-6 (2003).
Pi, et al., "Anomalies in water as obtained from computer simulations of the TIP4P/2005 model: density maxima, and density, isothermal compressibility and heat capacity minima," Molecular Physics 107(4-6), pp. 365-374 (2009).
Plata, et al., "An efficient and accurate framework for calculating lattice thermal conductivity of solids: AFLOW—AAPL Automatic Anharmonic Phonon Library," npj Computational Materials 3, 45, 10 pages (2017).
Plimpton, "Fast Parallel Algorithms for Short-Range Molecular Dynamics," Journal of Computational Physics 117(1), pp. 1-19 (1995).
Qiu, et al., "Is Water at the Graphite Interface Vapor-like or Ice-like?," The Journal of Physical Chemistry B 122(13), pp. 3626-3634 (2018).
Reddy, et al., "On the accuracy of the MB-pol many-body potential for water: Interaction energies, vibrational frequencies, and classical thermodynamic and dynamical properties from clusters to liquid water and ice," The Journal of Chemical Physics 145, 194504, 37 pages (2016).
Ren & Ponder, "Polarizable Atomic Multipole Water Model for Molecular Mechanics Simulation," The Journal of Physical Chemistry B 107(24), pp. 5933-5947 (2003).
Schiotz, et al., "Softening of nanocrystalline metals at very small grain sizes," Nature 391, pp. 561-563 (1998).
Shilling, et al., "Measurements for the vapor pressure of cubic ice and their implications for atmospheric ice clouds," Geophysical Research Letters 33(17), L17801, 5 pages (2006).
Skinner, et al., "The structure of water around the compressibility minimum," Journal of Chemical Physics 141, 214507, 7 pages (2014).
Skinner, et al., "The structure of water around the compressibility minimum," The Journal of Chemical Physics 141, 214507, 7 pages (2014).
Smith, et al., "Less is more: Sampling chemical space with active learning," The Journal of Chemical Physics 148, 241733, 24 pages (2018).
Soper, "The Radial Distribution Functions of Water as Derived from Radiation Total Scattering Experiments: Is There Anything We Can Say for Sure?," ISRN Physical Chemistry, 279463, 67 pages (2013).
Soper, "The Radial Distribution Functions of Water as Derived from Radiation Total Scattering Experiments: Is There Anything We Can Say for Sure?," International Scholarly Research Notices: Physical Chemistry 2013, 279463, 67 pages (2013).
Sosso, et al., "Crystal Nucleation in Liquids: Open Questions and Future Challenges in Molecular Dynamics Simulations," Chemical Reviews 116(12), pp. 7078-7116 (2016).
Stuart, et al., "A reactive potential for hydrocarbons with intermolecular interactions," The Journal of Chemical Physics 112, pp. 6472-6486 (2000).
Stukowski, "Visualization and analysis of atomistic simulation data with OVITO—the Open Visualization Tool," Modelling and Simulation in Materials Science and Engineering 18, 015012, 7 pages (2010).
Tersoff, "New empirical approach for the structure and energy of covalent systems," Physical Review B 37, pp. 6991-7000 (1988).
Togo & Tanaka, "First principles phonon calculations in materials science," Scripta Materlialia 108, pp. 1-5 (2015).
Ushio, "Factors affecting fast-ice break-up frequency in Lutzow-Holm Bay, Antarctica," Annals of Glaciology 44, pp. 177-182 (2006).
Vega & Abascal, "Relation between the melting temperature and the 406 temperature of maximum density for the most common models of water," Journal of Chemical Physics 123(14), 144504, 8 pages (2005).
Vega & Abascal, "Relation between the melting temperature and the temperature of maximum density for the most common models of water," The Journal of Chemical Physics 123, 144504, 8 pages (2005).
Vega & Abascal, "Simulating water with rigid non-polarizable models: a general perspective," Physical Chemistry Chemical Physics 13(44), pp. 19663-19688 (2011).
Vega, et al., "The melting temperature of the most common models of water," The Journal of Chemical Physics 122, 114507, 9 pages (2005).
Vega, et al., "What ice can teach us about water interactions: a critical comparison of the performance of different water models," Faraday Discussions 141, pp. 251-276 (2009).
Wang, et al., "Systematic Improvement of a Classical Molecular Model of Water," The Journal of Physical Chemistry B 117(34), pp. 9956-9972 (2013).
Warren, "Optical properties of snow," Reviews of Geophysics 20(1), pp. 67-89 (1982).
Weeks & Lee, "Observations on the Physical Properties of Sea-Ice at Hopedale, Labrador," Arctic 11(3), pp. 134-155 (1958).
Weikusat, et al., "Subgrain boundaries and related microstructural features in EDML (Antarctica) deep ice core," Journal of Geology 55(191), pp. 461-472 (2009).
Wellner, et al., "Distribution of glacial geomorphic features on the Antarctic continental shelf and correlation with substrate: implications for ice behavior," Journal of Glaciology 47(158), pp. 397-411 (2001).
Worby, et al., "East Antarctic Sea Ice: A Review of Its Structure, Properties and Drift," Antarctic Sea Ice: Physical Processes, Interactions and Variability 74, pp. 41-67 (1998).
Yen, "Review of Thermal Properties of Snow, Ice and Sea Ice," CRREL Report 81-10, 37 pages (1981).

\* cited by examiner

SYSTEMS AND METHODS FOR GENERATING PHASE DIAGRAMS FOR METASTABLE MATERIAL STATES

STATEMENT OF GOVERNMENT INTEREST

This invention was made with government support under Contract No. DE-AC02-06CH11357 awarded by the United States Department of Energy to UChicago Argonne, LLC, operator of Argonne National Laboratory. The government has certain rights in the invention.

TECHNICAL FIELD

The present invention relates generally to systems and methods of generating phase diagrams. Certain embodiments relate to generating phase diagrams for metastable states of materials.

BACKGROUND

Manufacturing and other processes may use phase diagrams to perform actions that depend on the state of materials under various conditions, such as temperature, pressure, or composition. Phase diagrams can provide information regarding states of materials at thermodynamic equilibrium, but may not provide information at states other than thermodynamic equilibrium.

SUMMARY

At least one aspect relates to a system. The system can include one or more processors configured to access at least one parameter of a material, generate a plurality of structures of the material using the at least one parameter, determine a state of each structure of the plurality of structures using the at least one parameter, determine a difference between the state of each structure of the plurality of structures and a ground state value, evaluate a convergence condition responsive to determining the difference between the state of each structure of the plurality of structures and the ground state value, and output at least one structure of the plurality of structures responsive to the convergence condition being satisfied.

At least one aspect relates to a method for generating phases for metastable states of materials. The method can include accessing, by one or more processors, at least one parameter of a material, generating, by the one or more processors, a plurality of structures of the material using the at least one parameter, determining, by the one or more processors, a state of each structure of the plurality of structures using the at least one parameter, determining, by the one or more processors, a difference between the state of each structure of the plurality of structures and a ground state value, evaluating, by the one or more processors, a convergence condition responsive to determining the difference between the state of each structure of the plurality of structures and the ground state value, and outputting, by the one or more processors, at least one structure of the plurality of structures responsive to the convergence condition being satisfied.

At least one aspect relates to a method. The method can include generating, by one or more processors, a plurality of candidate structures of a material, determining, by the one or more processors, an enthalpy of each candidate structure of the plurality of candidate structures, comparing, by the one or more processors, the enthalpy of each candidate structure to an energy threshold, selecting, by the one or more processors, a subset of the plurality of candidate structures, each candidate structure of the subset having an enthalpy less than the energy threshold, determining, by the one or more processors, a free energy of each candidate structure of the subset of the plurality of candidate structures for a plurality of temperature-pressure value pairs, determining, by the one or more processors, at least one boundary between phases represented by the subset of the plurality of candidate structures, and generating, by the one or more processors, a phase diagram data structure using the free energy of each candidate structure of the plurality of candidate structures and the at least one boundary.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

DETAILED DESCRIPTION

Figure 1:
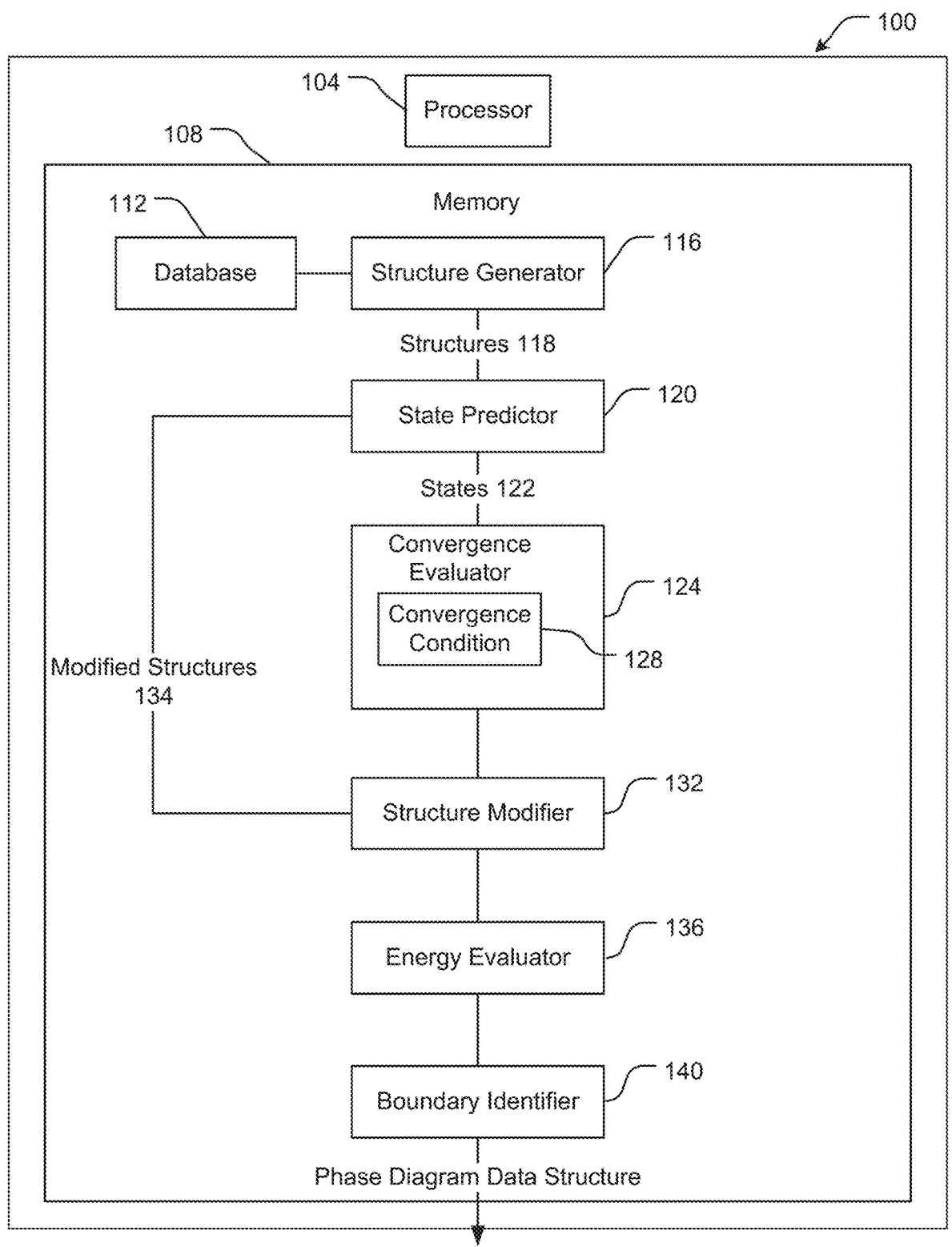
FIG. 1 is a block diagram of a metastable state phase diagram generation system.

Embodiments described herein relate generally to methods of generating metastable phase diagrams. Various technologies, including in material design and engineering, can involve using phase diagrams to identify properties of materials in order to perform processes using the identified properties. For example, heat can be applied to a system to cause a transition of the system from a first phase (e.g., solid phase) to a second phase (e.g., liquid phase).

A phase diagram can be represented using a data structure that maps one or more conditions of a material to one or more properties of the material. For example, the data structure can map values of temperature, pressure, and composition of the material to a corresponding free energy of the material. The phase diagram can be generated based on experimental data points that indicate boundaries between phases. Phenomenological models can be used to interpolate between available experimental data points, and to extrapolate to experimentally inaccessible regions (e.g., regions of temperature, pressure, and/or composition that cannot be achieved using experimentation).

However, such phase diagrams may provide information regarding materials at thermodynamic equilibrium, but not at other states that materials may reach. For example, during synthesis, in operation, or during processing, materials may not reach a state of thermodynamic equilibrium, but instead may achieve local minima (e.g., local minima of free energy), such as metastable states. The properties of materials in metastable states may be different than those in states of thermodynamic equilibrium (e.g., global minima). For example, nanoscale synthesis of diamond from graphite in a high pressure and high temperature (HPHT) anvil goes through a series of intermediate metastable phases. Although these phases can be experimentally observed through transmission electron microscopy (TEM) imaging, the exact temperature and pressure ranges at which these phases appear during the synthesis may not be known and may be computationally expensive to determine by calculating free energies for a large number of temperature and pressure values.

Systems and methods performed in accordance with the present solution can generate metastable states of materials using a predictive machine learning framework, which can predict, determine, and validate phase diagrams in chemical systems, including to detect metastable states, without relying on experimental information. For example, Monte Carlo Tree Search (MCTS) and evolutionary algorithms can be implemented to sample a free energy space of a chemical system as a function of temperature, pressure, and composition. The present solution can determine free energies of locally ergodic regions of the free energy space, which may otherwise be computationally non-trivial. The present solution can estimate or validate experimental conditions for synthesizing materials in metastable phases. The present solution can significantly reduce computational requirements for detecting metastable phases, such as by avoiding the need to compute free energy values for a large number of candidate structures at numerous temperature and pressure values (e.g., by instead identifying a relatively small number of candidate structures that are expected to be physically realistic at metastable phases). For example, temperature-pressure ranges at which a phase is likely to be stabilized and an estimate of excitation energies (from ΔG) to synthesize a metastable phase can be determined, enabling a systematic approach in designing experiments at favorable conditions for synthesis. The present solution can reproduce the dominant diamond and graphite phase in the equilibrium phase diagram, as well as predict the synthesizability of a metastable phase. Mapping the metastable phase diagram and inspecting the neighboring phases can provide insight into possible phase transformations pathways and help in selecting the appropriate starting material for the synthesis of a target phase to improve computer-aided materials discovery.

For example, a system in accordance with the present solution can include one or more processors that access an input data structure regarding a material. The input data structure can include an identifier of the material and at least one parameter of the material, such as temperature, pressure, or composition. The one or more processors can generate a plurality of structures of the material. The one or more processors can determine a state of each structure using the at least one parameter. The one or more processors can determine an error of the each state, and evaluate a convergence condition using the error. The one or more processors can modify the plurality of structures responsive to the convergence condition not being satisfied. The one or more processors can output the states of the structures responsive to the convergence condition being satisfied.

FIG. 1 depicts a system 100 for generating phase diagrams for metastable states of materials. The system 100 includes one or more processors 104 and memory 108, which can be implemented as one or more processing circuits. The processor 104 may be a general purpose or specific purpose processor, an application specific integrated circuit (ASIC), one or more field programmable gate arrays (FPGAs), a group of processing components, or other suitable processing components. The processor 104 may be configured to execute computer code or instructions stored in memory 108 (e.g., fuzzy logic, etc.) or received from other computer readable media (e.g., CDROM, network storage, a remote server, etc.) to perform one or more of the processes described herein. The memory 108 may include one or more data storage devices (e.g., memory units, memory devices, computer-readable storage media, etc.) configured to store data, computer code, executable instructions, or other forms of computer-readable information. The memory 108 may include random access memory (RAM), read-only memory (ROM), hard drive storage, temporary storage, non-volatile memory, flash memory, optical memory, or any other suitable memory for storing software objects and/or computer instructions. The memory 108 may include database components, object code components, script components, or any other type of information structure for supporting the various activities and information structures described in the present disclosure. The memory 108 may be communicably connected to the processor 104 and may include computer code for executing (e.g., by processor 104) one or more of the processes described herein. The memory 108 can include various modules (e.g., circuits, engines) for completing processes described herein. The one or more processors 104 and memory 108 may include various distributed components that may be communicatively coupled by wired or wireless connections; for example, various portions of system 100 may be implemented using one or more client devices remote from one or more server devices. The memory 108 can include various software or firmware engines, modules, scripts, databases, or other computer code to implement the various components described herein, including the database 112, structure generator 116, state predictor 120, convergence evaluator 124, structure modifier 132, energy evaluator 136, boundary identifier 140, or features or functions thereof. For example, the database 112, structure generator 116, state predictor 120, convergence evaluator 124, structure modifier 132, energy evaluator 136, boundary identifier 140 can be or include any function, operation, routine, logic, or instructions to perform functions described herein.

The system 100 can include a database 112. The database 112 can include input data structures regarding materials for which metastable phases are to be determined. The input data structure can include an identifier of the material and one or more parameters of the material. The identifier of the material can include identifiers of each atom, molecule, or chemical compound of the material, which can be used to retrieve properties of the material (e.g., properties that can be used to determine free energy of the material). The parameters of the material can include parameters such as temperature, pressure, and composition. The input data structure may include a state value corresponding to the one or more parameters of the material, such as enthalpy or free energy, which may be used for validating state values determined by the system 100. For example, the input data structure may include a free energy value determined through experimentation in order to validate outputs of the system 100. The input data structure may include various values of parameters (e.g., various values of temperature, pressure, and composition) of the material, which may be assigned corresponding values of free energy.

The system 100 can include a structure generator 116. The structure generator 116 can generate a structure 118 of the material using the one or more parameters of the material. The structure generator 116 may randomly generate the structure. The structure 118 can be a chemical structure of the material. For example, the structure 118 can represent one or more bonds between atoms or molecules of the material. The structure 118 can represent packing structures, layers, or other arrangements of the material. The structure 118 can be a crystal structure. As examples for a material that includes carbon, the structures 118 may include any of a variety of graphite structures (including but not limited to cubic, cubic first neighbor, cubic second neighbor, hexagonal, hexagonal first neighbor, or hexagonal second neighbor structures for graphite), diamond structures, or amorphous structures. The structure generator 116 can (randomly) generate N structures 118 for the material, for which state information (e.g., enthalpy, free energy) can be determined and used to confirm convergence of the structures 118 or trigger modification of the structures 118.

The structure generator 116 can generate a plurality of structures 118 (e.g., candidate structures) using the one or more parameters of the material. For example, the structure generator 116 can use the one or more parameters to determine lengths of bonds between atoms of the material, spacing of atoms, arrangements of atoms or molecules, or other features of the structure 118. The structure generator 116 can use various models, rules, or policies to determine the structure 118. For example, the structure generator 116 can use rules based on atomic volume, minimum bond length, and maximum bond length constraints to determine the structure 118.

The system 100 can include a state predictor 120. The state predictor 120 can determine a state 122 of each structure 118. For example, the state predictor 120 can determine the state 122 of each structure 118 using the structure 118 and the one or more parameters of the material. The state predictor 120 can determine the state 122 to be or include an enthalpy or free energy of the material using the structure 118 and the one or more parameters of the material.

The state predictor 120 can determine the state 122 of the structure 118 using various models. For example, the state predictor 120 can use a classical potential model to determine the state 122, which can model forces between atoms or molecules using the one or more parameters of the material to determine the state 122 (e.g., by performing a molecular dynamics simulation). The state predictor 120 can use a density functional theory (DFT) model to determine the state 122.

The state predictor 120 can determine the state 122 at a particular set of parameters. For example, the state predictor 120 can determine state 122 for the structure 118 at a temperature of zero Kelvin and one or more pressures (e.g., determine enthalpy $H(T=0, P)$). The state predictor 120 can maintain in the database 112 data including the state 122 of the structure 118 for the corresponding one or more parameters (e.g., enthalpy at a particular temperature and pressure for the structure 118), which can increase the speed of searching for minimas and avoid sampling of unphysical configurations. By using the state predictor 120 to determine the state as an enthalpy at $T=0$, the system 100 can more efficiently evaluate a large number of structures 118 to identify the structures 118 that are most likely to be physically realistic for achieving a metastable phase, particularly a metastable phase that can be reached during synthesis of the material (e.g., by perturbing the material using laser energy).

The state predictor 120 can assign a rank to each of the N structures 118 using the state 122 of the respective structure 118 (e.g., using enthalpy of each structure 118). The state predictor 120 can assign relatively high ranks to structures 118 with relatively low state values, and relatively low ranks to structures with relatively high state values, as the state values can represent a stability of the structure 118 or a likelihood of the structure 118 being physically possible at the corresponding pressure (and temperature).

The state predictor 120 can determine a selection probability score for the structure 118. The selection probability score can indicate a fitness of the structure 118, which can be used for modifying the structure 118 (e.g., for genetic operations described herein). The state predictor 120 can determine the selection probability score using the state 122 of the structure 118, such as to determine a relatively higher probability for relatively lower state values. The state predictor 120 can determine the selection probability score using the rank assigned to the structure 118, such as by applying the rank as an input to a mapping data structure (e.g., lookup table) or function that outputs the selection probability score responsive to the rank.

The system 100 can include a convergence evaluator 124. The convergence evaluator 124 can determine whether the states 122 of the structures 118 satisfy one or more convergence conditions, in order to determine whether to output the structures 118 or modify the structures 118. The convergence condition 128 can include one or more rules, policies, heuristics, functions, or thresholds that the convergence evaluator 124 can use to determine that the structures 118 have converged.

The convergence condition 128 can include a threshold, such as an energy threshold or enthalpy threshold. The threshold can represent an energy cutoff above which structures would not be expected to form as a metastable state. The threshold may be based on an excitation energy, such as expected amount of energy that can be provided from an external source (e.g., laser) to perturb the material from a structure at thermal equilibrium (e.g., at a ground state, such as having an enthalpy of zero) to a metastable structure. As such, the threshold may represent whether it is physically realistic for a particular structure 118 to be achieved as a metastable structure of the material (e.g., the closer the enthalpy of the particular structure 118 is to the ground state, the more likely it is that the material will form the particular structure 118). For example, the threshold may be on the order of 100 meV/atom to 1 eV/atom. The threshold may be greater than 300 meV/atom and less than 800 meV/atom. The threshold may be greater than 500 meV/atom and less than 750 meV/atom. The threshold may be 670 meV/atom. The threshold may be adjusted to be lower to reduce the number of structures 118 selected or increased to evaluate metastable phases at high excitation energies. If the state (e.g., enthalpy, free energy) of the ground state is greater than zero, the state of the ground state may be summed with the threshold for comparing with the states 122 of the structures 118.

The convergence evaluator 124 can determine the convergence condition 128 to be satisfied responsive to the state 122 of at least a subset of the structures 118 being less than the threshold. The convergence evaluator 124 can select the subset of the structures 118, compare each state 122 of the corresponding structure 118 of the subset to the threshold, and determine the convergence condition 128 to be satisfied responsive to the state 122 of each structure 118 of the subset being less than the threshold (or less than or equal to the threshold). For example, the convergence evaluator 124 can determine the convergence condition 128 to be satisfied responsive to one half, one quarter, one eighth, one tenth, or various other subsets of the structures 118 to have states 122 that are less than the threshold (e.g., N/2, N/4, N/8, N/10, etc.).

The system 100 can include a structure modifier 132. The structure modifier 132 can modify the structures 118 to generate modified structures 134. The structure modifier 132 can use features of the structures 118, such as atoms, groups of atoms, or bonds between atoms or molecules, to generate the modified structures 134. The structure modifier 132 can use the structures 118 as parent structures to generate the modified structures 134 as child structures. The structure modifier 132 may select a subset of the structures 118 to use for modification using the selection probability score assigned to each structure by the state predictor 120, such that structures 118 that are more likely to be physically realistic (e.g., have lower state values) are more likely to be used to generate candidate structures for evaluation in subsequent iterations.

The structure modifier 132 can apply one or more genetic operations to the structures 118 to generate the modified structures 134, such as to combine features from structures 118 to generate the modified structures 134. The structure modifier 132 can apply a crossover operation to generate the modified structure 134 to include features of at least two parent structures 118. The structure modifier 132 can apply a mutation operation to generate the modified structure 134 to include at least one randomly modified (e.g., mutated) feature relative to the parent structure 118. For example, the structure modifier 132 can mutate features such as atomic position or cell parameters to generate the modified structure 134.

The structure modifier 132 can provide the modified structures 134 to the state predictor 120. The state predictor 120 can determine the state values (e.g., enthalpy, free energy) of the modified structures 134, enabling the system 100 to iteratively evaluate structures 118 and modify the structures 118 (by generating modified structures 134) until the structures 118 have converged. The structures 118 that converge can represent metastable phases of the material.

The system 100 can include an energy evaluator 136. The energy evaluator 136 can incorporate features of the state predictor 120. The energy evaluator 136 can receive the structures 118 that satisfied the convergence condition 128 (e.g., had enthalpies less than the cutoff enthalpy) and determine a free energy (e.g., Gibbs free energy) of each received structure 118. The energy evaluator 136 can assign the free energy values to the structures 118 in the database 112. The energy evaluator 136 can determine the free energy for various temperature-pressure value pairs.

The energy evaluator 136 may group the received structures 118 into one or more groups, which can reduce the number of candidate structures for which free energy is to be determined, and thus reduce computations to be performed by the energy evaluator 136. The energy evaluator 136 can group the structures 118 using characteristics such as radial distribution function and angular distribution function. For example, hexagonal graphite, orthorhombic graphite, and rhombohedral graphite may be grouped together, and the energy evaluator 136 can assign a same free energy value to each of the structures 118 of the group based on determining the free energy value for one of the structures 118 of the group.

The energy evaluator 136 can use various models, functions, or other algorithms to determine the free energy of the structures 118. The energy evaluator 136 can determine the free energy at various (discretized) points in [temperature, pressure] space (even as the states 122 determined by the state predictor 120 are for a temperature of zero Kelvin). The energy evaluator 136 may determine a volume of the structure 118 based on temperature and pressure, and use the volume to determine the free energy. The energy evaluator 136 may determine a vibrational free energy of the structure 118, such as to facilitate determining entropy of the structure 118 (e.g., a −temperature times entropy term in the Gibbs free energy calculation) to be approximated using the vibrational free energy. The energy evaluator 136 can determine the enthalpy at a given temperature and pressure using a molecular dynamics model, such as by equilibrating under an isothermal-isobaric ensemble (e.g., NPT ensemble), and determine the entropic part of the free energy from a phonon spectra computation. The phonon spectra and the corresponding vibrational free energies can be determined at the equilibrium density obtained from molecular dynamics simulations. The energy evaluator 136 can perform the molecular dynamics simulations using Large-scale Atomic/Molecular Massively Parallel Simulator (LAMMPS) and the phonon spectra using PHONOPY.

The system 100 can generate a phase diagram data structure that assigns the free energy values determined by the energy evaluator 136 to corresponding values of temperature and pressure. For example, each data point of the phase diagram data structure may include an identifier of the structure, a temperature, a pressure, and a free energy. The system 100 can identify metastable phases (along with equilibrium phases) by parsing the phase diagram data structure using a free energy value. For example, for a particular free energy value, the system 100 can identify, for one or more sets of temperature and pressure values, the corresponding phase assigned to the temperature and pressure values for which the free energy determined by the energy evaluator 136 is greater than or equal to the particular free energy value. For example, for a given temperature and pressure, there may be multiple phases possible for the structure, depending on the free energy value; as the free energy is adjusted from zero through the cutoff energy value (e.g., the threshold of convergence condition 128), various phases may be identified based on whether the free energy for the phase is greater than or equal to the adjusted free energy.

The system 100 can include a boundary identifier 140. The boundary identifier 140 can determine boundaries between data points representing phases of the phase diagram data structure, including between metastable phases. The boundary identifier 140 can include a classifier, such as a support vector machine (SVM), that receives the phase diagram data structure as input and classifies the data points of the phase diagram data structure based on the phases of the data points to generate boundaries between phases. The boundary identifier 140 may use a multiclass SVM that does not use decomposition, such as a non-homogenous fourth-order polynomial kernel, to classify the phases of the phase diagram data structure. By using a single SVM, the boundary identifier 140 can reduce computational requirements for determining the boundaries. The boundaries determined by the boundary identifier 140 can indicate the phase of the material under particular conditions (e.g., temperature, pressure, composition), including for values of conditions for which free energies have not been explicitly determined.

The system 100 can use the boundaries identified by the boundary identifier 140 to output a phase of a material responsive to receiving parameters of the material. For example, the system can receive a temperature, pressure, and free energy of a material, and apply the boundary to the temperature, pressure, and free energy to determine the phase of the material (including for metastable phases at free energies greater than zero).

Figure 2A:
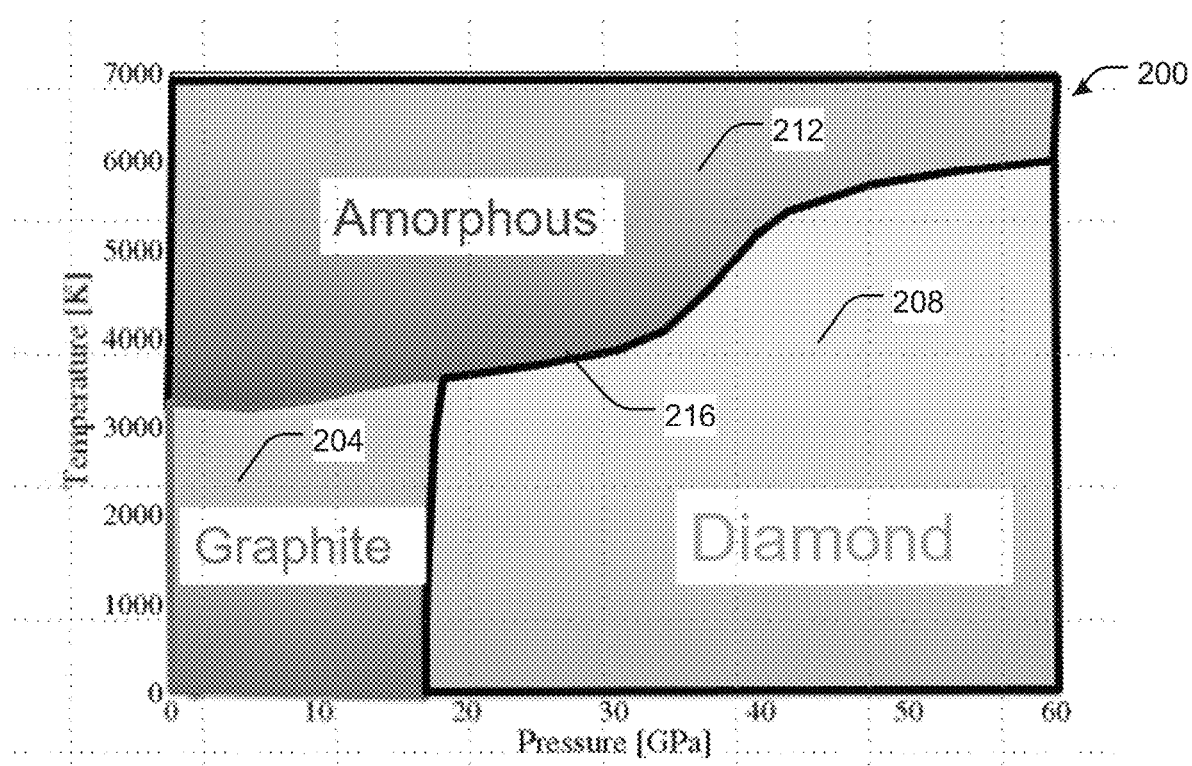
FIGS. 2A-2C depict charts of an equilibrium state and metastable states of a material.
Figure 2B:
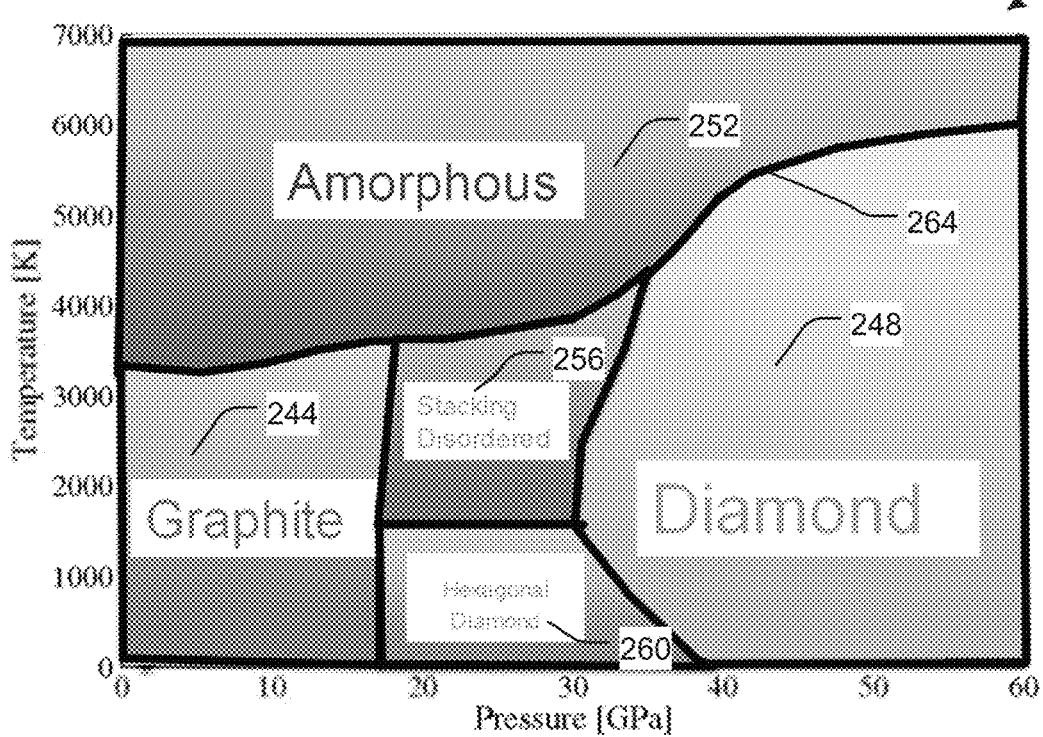
Figure 2C:
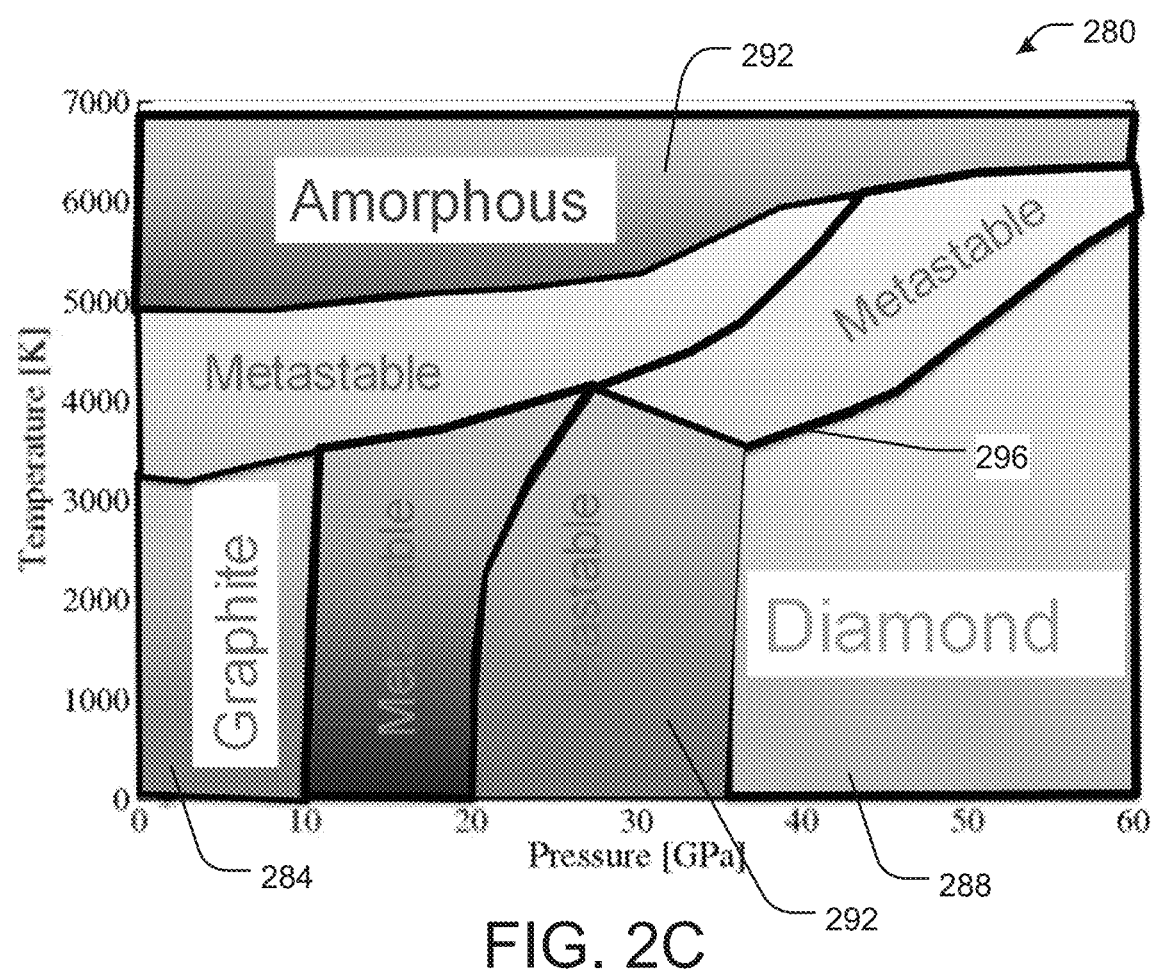

FIGS. 2A-2C depict phase diagrams 200, 240, 280 for carbon at various free energy levels for temperatures ranging from 0 to 7000 Kelvin and pressures ranging from 0 to 60 GPa. The phase diagrams 200, 240, 280 can be generated in accordance with features of the system 100. The phase diagram 200 can be for carbon at thermal equilibrium (e.g., $\Delta G$=zero), and indicates that carbon can be in graphite 204, diamond 208, or amorphous 212 phases under various temperature and pressure conditions. In addition, the phase diagram 200 includes boundaries 216 between the phases, which can be determined using the boundary identifier 140, enabling determination of the phase of carbon even for temperatures and pressures for which free energy (and phase information) has not been explicitly determined through experimentation or direct computation. For example, the system 100 may not include a data point having a free energy value assigned to a temperature of 2000 Kelvin and a pressure of 20 GPa (e.g., as determined through experimentation or computation using a free energy function), but the system 100 can output a prediction indicating the phase to be diamond for the temperature of 2000 Kelvin and the pressure of 20 GPa using the phase diagram 200 (and the boundaries 216 thereof).

The phase diagram 240 indicates phases for carbon at metastable states having a free energy of $\Delta G$=10 meV/atom. The phase diagram 240 identifies graphite 244, diamond 248, and amorphous 252 phases, as well as phases not identified by the phase diagram 200, including stacking disordered 256 and hexagonal diamond 260 phases. The phase diagram 240 includes boundaries 264 between phases. As compared to the phase diagram 200, which indicates the phase to be diamond for the temperature of 2000 Kelvin and the pressure of 20 GPa, the phase diagram 240 indicates the phase to be the metastable stacking disordered 256 phase for the temperature of 2000 Kelvin and the pressure of 20 GPa.

The phase diagram 280 indicates phases for carbon at metastable states having a free energy of $\Delta G$=100 meV/atom. The phase diagram 280 identifies graphite 284, diamond 288, and amorphous 292 phases, as well as phases not identified by the phase diagram 200, including several metastable phases, including metastable phase 296. The phase diagram 240 includes boundaries 298 between phases. As compared to the phase diagram 200, which indicates the phase to be diamond for the temperature of 2000 Kelvin and the pressure of 20 GPa, the phase diagram 280 indicates the phase to be the metastable phase 296 for the temperature of 2000 Kelvin and the pressure of 20 GPa. The phase diagrams 240, 280 thus represent slices of the temperature-pressure-free energy space (which has been classified into different phases depending on temperature, pressure, and free energy) at various free energies corresponding to potential metastable energy levels.

Figure 3:
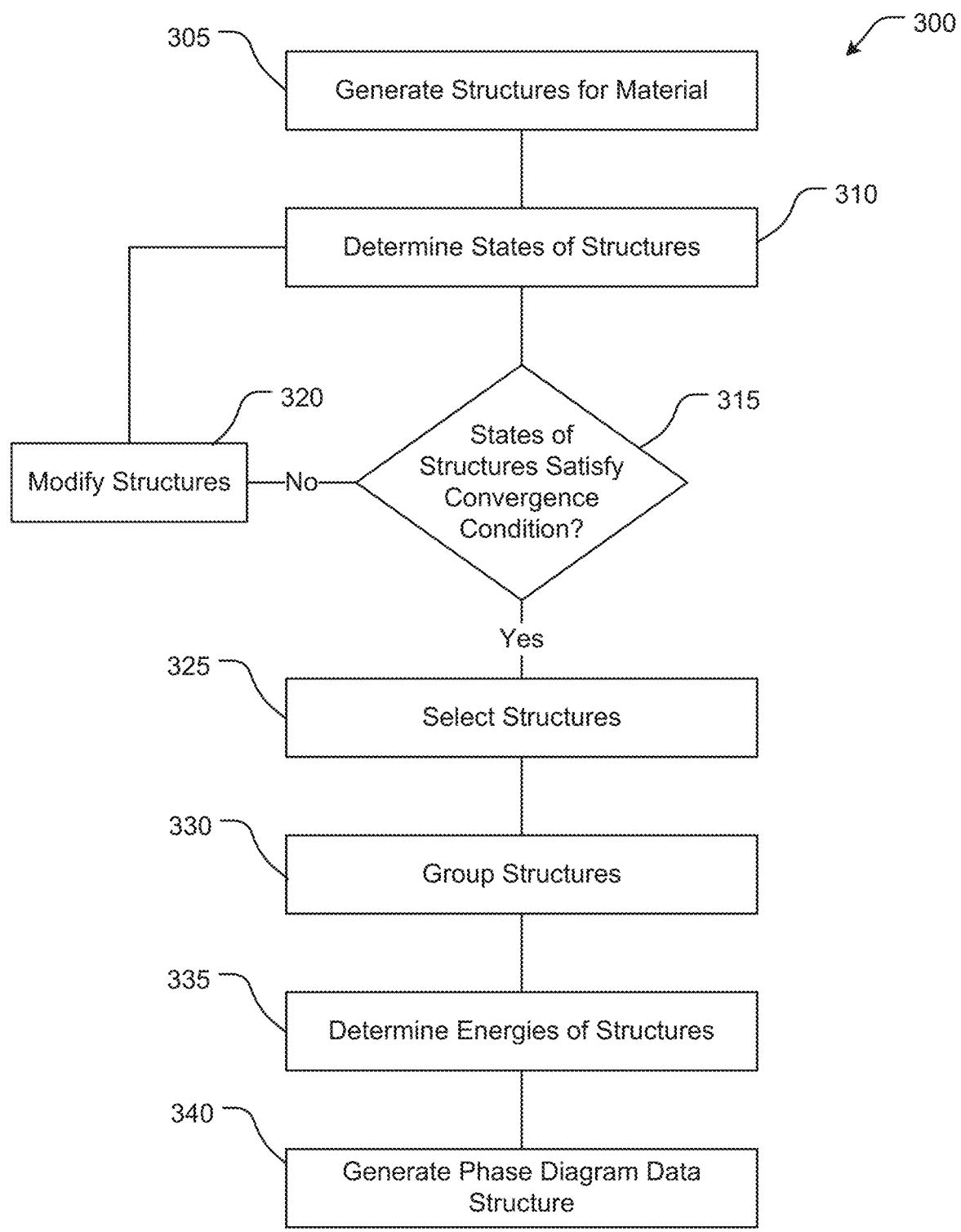
FIG. 3 is a flow diagram of a method for metastable state phase diagram generation.

FIG. 3 depicts a method 300 for generating phase diagrams for metastable phases of materials. The method 300 can be performed using various systems and components described herein, such as the system 100. The method 300 can be performed to determine and control process conditions for synthesizing materials at metastable phases, such as to determine temperature and pressure for causing a material to achieve a selected metastable phase.

At 305, structures of a material are generated. The structures can be randomly generated, such as for a first iteration of structure generation. The structures can be a chemical structure of the material. For example, the structures can represent one or more bonds between atoms or molecules of the material. The structures can represent packing structures, layers, or other arrangements of the material. The structures can be a crystal structure. N structures can be generated for the material.

The structures can be generated using one or more parameters of the material, such as composition, temperature, and pressure. The structures can be generated using the one or more parameters and various models, rules, or policies. For example, the structures can be generated based on atomic volume, minimum bond length, and maximum bond length constraints. The structures can be generated to indicate bonds between atoms and the lengths of the bonds between atoms.

At 310, states of the structures are determined. The states of a particular structure can be determined by applying the one or more parameters of the material and the particular structure as input to one or more of various models. The state can be determined to include an enthalpy or a free energy of the particular structure.

For example, the enthalpy can be determined by using temperature, pressure, and the particular structure as inputs to a classical potential model or a DFT model. The enthalpy may be determined at parameters of temperature=zero Kelvin and at various pressures. The enthalpy can be assigned to a data structure representative of the particular structure, which may later be queried for generating a phase diagram.

The structures can be ranked using the states of the structures. Structures having relatively higher state values (e.g., relatively higher enthalpies or free energies) may be assigned relatively lower ranks, and vice versa, in order to identify structures that are closest to ground state (and thus more likely to be physically realistic).

A selection score (e.g., selection probability score) can be assigned to the particular structure using at least one of the state of the particular structure or the rank assigned to the particular structure. The selection score can be used to determine whether to use the structure or features or portions thereof for generating future generations of structures to evaluate. Relatively higher selection scores can be assigned to structures having relatively higher ranks (e.g., having relatively lower state values, such as relatively lower enthalpies). The selection score can be determined by applying the rank or state value as an input to a mapping data structure (e.g., lookup table) or function that outputs the selection probability score responsive to the rank or state value.

At 315, it is determined whether the states of the structures satisfy a convergence condition. The convergence condition can include a threshold that represents an energy cutoff above which structures would not be expected to form as a metastable state. The threshold may be based on an excitation energy, such as expected amount of energy that can be provided from an external source (e.g., laser) to perturb the material from a structure at thermal equilibrium (e.g., at a ground state, such as having an enthalpy of zero) to a metastable structure.

The state value of the structures (e.g., value of at least one of enthalpy or free energy) can be compared to the threshold. The threshold can be determined to be satisfied for a particular structure responsive to the state value for the structure being less than (or less than or equal to) the threshold. The convergence condition can be determined to be satisfied responsive to at least a subset of the particular structures having state values that satisfy the threshold. For example, the structure generation and modification processes described herein can use a number N of structures on the order of tens or hundreds, many of which may have relatively high state values. By determining convergence condition to be satisfied responsive to a subset of the N total structures to have state values less than the threshold, a sufficient number of structures for metastable phases and phase diagram generation can be identified without requiring excessive iterations through the process. The number of structures to be determined for a sufficiently large subset can include N/2, N/4, N/8, N/10, etc. structures. For example, one hundred structures can be initially (e.g., randomly) generated, and the convergence condition can be determined to be satisfied responsive to identifying ten structures for which the at least one of the enthalpy or free energy is less than the energy cutoff.

At 320, responsive to the convergence condition not being satisfied (e.g., not enough structures were determined to have enthalpies or free energies less than a corresponding cutoff threshold), one or more structures can be modified to generate modified structures. The modified structures can be generated by modifying features of the structures such as bonds, bond lengths, atoms, or groups of atoms.

Structures can be selected for modification using the selection score. For example, a relatively higher selection score may indicate that a structure is a better candidate to have its features included in the modified structures for evaluation in future iterations. Structures can be selected for modification by randomly selecting structures based on respective selection scores.

As depicted in FIG. 3, the states of the modified structures can be determined responsive to generating the modified structures. A number of modified structures may be less than N, such that at least some of the structures from the previous generation may be used for further evaluation. The structures used from the previous generation may be selected based on the respective selection scores, or based on being structures having state values less than the threshold (e.g., once a structure is determined to have a state value less than the threshold, it may be held for later processing, and subsequent iterations can be used to search for fewer additional structures that satisfy the threshold).

The structures may be modified using one or more genetic operations, such as to combine features from structures to generate the modified structures. A crossover operation can be applied to generate a modified structure to include features of at least two parent structures. A mutation operation can be applied to generate a modified structure to include at least one randomly modified (e.g., mutated) feature relative to the parent structure. For example, features such as atomic position or cell parameters can be modified to generate the modified structure.

At 325, responsive to the convergence condition being satisfied, structures can be selected for use for metastable phases. For example, each structure (e.g., of the subset) for which the state value is less than or equal to the threshold can be selected.

At 330, at least some of the selected structures can be assigned to a group. The group may include structures that are similar, such that a first free energy can be determined for a first structure of a group and assigned to each remaining structure of the group, reducing a number of total free energy calculations to be performed. Structures can be assigned to groups using characteristics such as radial distribution function and angular distribution function.

At 335, energies (e.g., free energies) of the selected structures can be determined. Various models, functions, or other algorithms to determine the free energy. The free energy can be determined at various (discretized) points in [temperature, pressure] space. A volume of the structure can be determined based on temperature and pressure, and used to determine the free energy. A vibrational free energy of the structure can be determined, such as to facilitate determining entropy of the structure (e.g., a −temperature times entropy term in the Gibbs free energy calculation) to be approximated using the vibrational free energy. The enthalpy of the structure can be determined at a given temperature and pressure using a molecular dynamics model, such as by equilibrating under an isothermal-isobaric ensemble (e.g., NPT ensemble), and to determine the entropic part of the free energy from a phonon spectra computation (e.g., where free energy G=enthalpy H−temperature T times entropy S). The phonon spectra and the corresponding vibrational free energies can be determined at the equilibrium density obtained from molecular dynamics simulations. The molecular dynamics simulations can be performed using Large-scale Atomic/Molecular Massively Parallel Simulator (LAMMPS) and the phonon spectra performed using PHONOPY.

At 340, a phase diagram data structure can be generated using the energies of the selected structures. The phase diagram data structure can include data points indicating variables such as temperature, pressure, composition, free energy (e.g., difference in free energy relative to ground state), and structure or phase (including identifiers for metastable phases or the associated structures). Generating the phase diagram data structure can include determining boundaries between phases, such as by using a classifier (e.g., SVM) to classify the data points based on phases.

Generating the phase diagram data structure can include providing phase information at a particular free energy or range of free energies, such as indicating which phases (e.g., structures) correspond to particular values of temperature and pressure at the particular free energy or range of free energies. For example, a free energy of 10 meV/atom can be used as an input to identify metastable phases at various values of temperature and pressure for the free energy of 10 meV/atom.

Various processes and devices can be operated using the metastable phase information represented by the phase diagram data structure. For example, to synthesize a material to be in a particular metastable phase, the phase diagram data structure can be searched to identify the metastable phase, and the temperature and pressure associated with the particular metastable phase can be retrieved. A reaction or other process to synthesize the material can be controlled to operate at the retrieved temperature and pressure, and an energy source (e.g., laser) can be applied to the material to modify the material from a ground state phase (e.g., thermal equilibrium phase) to the metastable phase. In addition, experimentation can be validated or supplemented using the phase diagram data structure. For example, a structure of a material in a metastable phase can be identified through imaging (but for which parameter data, such as temperature and pressure information, is not available). The phase diagram data structure can be parsed to identify the structure corresponding to the structure identified through imaging, and the temperature(s) and pressure(s) corresponding to the structure identified in the phase diagram data structure can be retrieved.

Definitions

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

The term "coupled," as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. Such members may be coupled mechanically, electrically, and/or fluidly.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device, etc.) may include one or more devices (e.g., RAM, ROM, Flash memory, hard disk storage, etc.) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit and/or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the fluid control systems and methods of fluid control as shown in the various exemplary embodiments is illustrative only. Additionally, any element disclosed in one embodiment may be incorporated or utilized with any other embodiment disclosed herein. Although only one example of an element from one embodiment that can be incorporated or utilized in another embodiment has been described above, it should be appreciated that other elements of the various embodiments may be incorporated or utilized with any of the other embodiments disclosed herein.

The invention claimed is:

1. A system, comprising:
   one or more processors configured to:
   access at least one parameter of a material;
   generate a plurality of structures of the material using the at least one parameter;

determine a state of each structure of the plurality of structures using the at least one parameter;

determine a difference between the state of each structure of the plurality of structures and a ground state value;

evaluate a convergence condition responsive to determining the difference between the state of each structure of the plurality of structures and the ground state value; and output at least one structure of the plurality of structures responsive to the convergence condition being satisfied.

2. The system of claim 1, wherein the one or more processors the one or more processors are configured to output a phase diagram data structure representing the at least one structure.

3. The system of claim 2, wherein the state of each structure of the plurality of structures comprises an enthalpy of the structure, and the one or more processors are configured to:

compare the enthalpy of each structure to an energy threshold;

select a subset of the plurality of structures, each structure of the subset having an enthalpy less than the energy threshold;

determine a free energy of each structure of the subset for a plurality of temperature-pressure value pairs; and apply a classifier to the phase diagram data structure to determine one or more boundaries between phases of the phase diagram data structure based on the free energy of each structure of the subset.

4. The system of claim 1, wherein the at least one parameter comprises at least one of a temperature, a pressure, or a composition of the material.

5. The system of claim 1, wherein the state of each structure comprises an enthalpy of the structure, and the one or more processors are configured to determine the state of each structure by providing the structure and the at least one parameter as input to a density functional theory model.

6. The system of claim 1, wherein the one or more processors are configured to modify the plurality of structures by applying a genetic function to the plurality of structures.

7. The system of claim 1, wherein the one or more processors are configured to modify one or more first structures of the plurality of structures of the material responsive to the convergence condition not being satisfied.

8. The system of claim 7, wherein the one or more processors are configured to modify the one or more first structures by applying a genetic operation to the one or more first structures.

9. The system of claim 7, wherein the one or more processors are further configured to:

assign a selection score to each of the one or more first structures based on a respective state of the one or more first structures; and modify each of the one or more first structures based on the selection score assigned to the corresponding first structure.

\* \* \* \* \*